(12) United States Patent
Katayama et al.

(10) Patent No.: US 10,174,058 B2
(45) Date of Patent: Jan. 8, 2019

(54) VINYL SILANE COMPOUND

(71) Applicant: Shin-Etsu Chemical Co., Ltd., Tokyo (JP)

(72) Inventors: Taiki Katayama, Annaka (JP); Masayuki Ikeno, Annaka (JP); Misaki Takai, Annaka (JP); Takafumi Sakamoto, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 15/757,873

(22) PCT Filed: Aug. 22, 2016

(86) PCT No.: PCT/JP2016/074322
§ 371 (c)(1),
(2) Date: Mar. 6, 2018

(87) PCT Pub. No.: WO2017/043294
PCT Pub. Date: Mar. 16, 2017

(65) Prior Publication Data
US 2018/0334467 A1    Nov. 22, 2018

(30) Foreign Application Priority Data

Sep. 8, 2015  (JP) ................. 2015-176907

(51) Int. Cl.
| C07F 7/08 | (2006.01) |
| C07F 7/00 | (2006.01) |
| C08L 83/05 | (2006.01) |
| C08G 77/50 | (2006.01) |

(52) U.S. Cl.
CPC .............. *C07F 7/0805* (2013.01); *C07F 7/08* (2013.01); *C07F 7/0832* (2013.01)

(58) Field of Classification Search
CPC .......... C07F 7/805; C07F 7/825; C07F 7/827; C07F 7/0832; C07F 7/08; C07K 5/54; C08G 77/50
See application file for complete search history.

(56) References Cited

U.S. PATENT DOCUMENTS

| 7,897,715 B1 | 3/2011 | Laskoski et al. |
| 2004/0106004 A1 | 6/2004 | Li |
| 2014/0275445 A1 | 9/2014 | Yamanaka et al. |

FOREIGN PATENT DOCUMENTS

| JP | 11-246769 A | 9/1999 |
| JP | 2004-182737 A | 7/2004 |
| JP | 2013-108063 A | 6/2013 |
| WO | WO 2011/129935 A1 | 10/2011 |

OTHER PUBLICATIONS

Kunio Ito, "Silicone Handbook" Nikkan Kogyo Shimbun, Ltd. (first impression of the first edition), Aug. 31, 1990, 13 Pages (with English language translation).
Monika Ludwiczak, et al., "Stereoselective synthesis and luminescence properties of novel trans-regular N-alkylcarbazolylene-silylene-vinylene polymers" Journal of Organometallic Chemistry, vol. 750, 2014, pp. 150-161.
Yujiro Itami, et al., "Novel Organosilicon Starburst Compounds Based on Ruthenium-Catalyzed Silylative Coupling Reactions of 1,3,5-Tris(dimethylvinylsilyl)benzene" Organometallics, vol. 22, No. 9, 2003, pp. 1835-1842.
Robert D. Kelly, et al., "Synthesis and spectroscopic characteristics of bis(ethenyldimethylsilylmethyl)platinum(II) complexes containing nitrogen donor ligands" Journal of Organometallic Chemistry, vol. 361, 1989, pp. 123-138.
Von Gerd Greber, et al., "Oligomeric Silicon Compounds with Functional Groups. XVIII. Preparation and polyaddition reactions of 1,1-bis-(dimethylhydrosilylmethyl) ferrocene" Makromolekulare Chemie, vol. 104, 1967, 14 Pages (with English language summary).

*Primary Examiner* — Jafar F Parsa
(74) *Attorney, Agent, or Firm* — Oblon, McClelland, Maier & Neustadt, L.L.P.

(57) ABSTRACT

Provided is a compound for imparting a thermal plasticity to an organic silicon resin. The compound is a novel vinyl silane compound represented by the following formula (1):

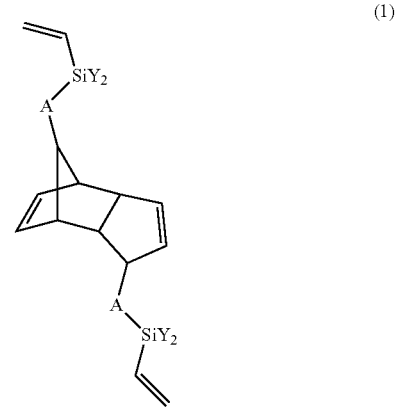

(1)

wherein A independently represents a divalent hydrocarbon group having 1 to 6 carbon atoms; Y independently represents a substituted or unsubstituted monovalent hydrocarbon group having 1 to 12 carbon atoms.

12 Claims, 1 Drawing Sheet

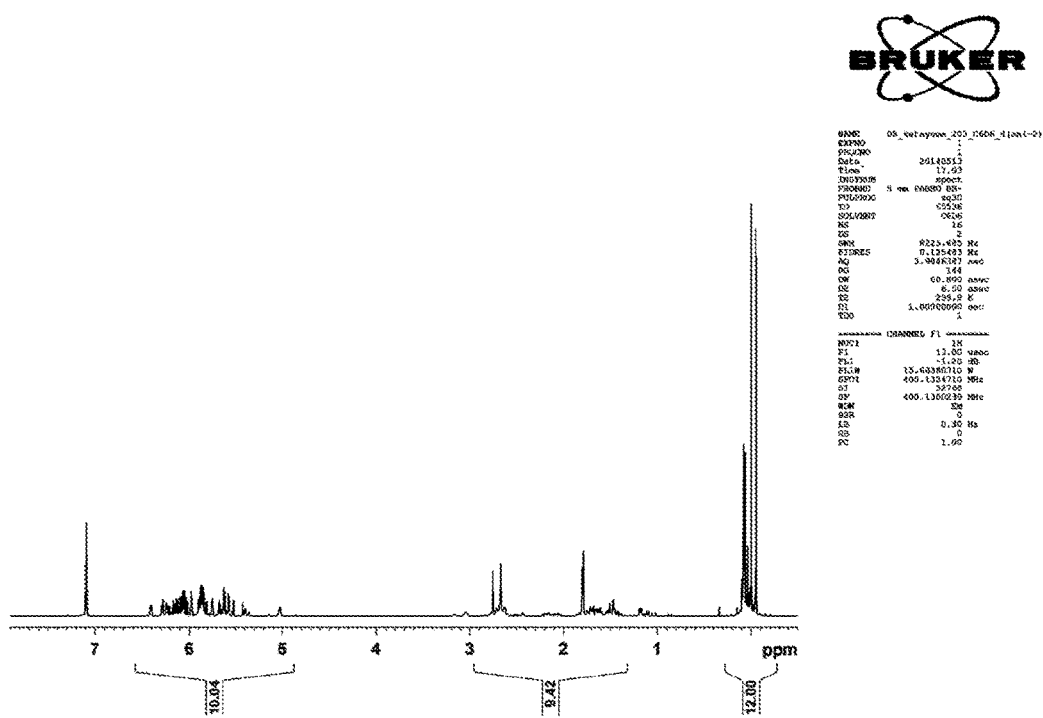

VINYL SILANE COMPOUND

TECHNICAL FIELD

The present invention relates to a novel vinyl silane compound, especially to: a vinyl silane compound capable of being reversibly changed between a dimer and a monomer by heat; and a method for producing the same.

BACKGROUND ART

Conventionally, as a vinyl silane compound having two vinylsilyl groups in one molecule (particularly, a vinyldiorganosilyl group such as a vinyldimethylsilyl), there have been known, for example, 1,3-divinyl-1,1,3,3-tetramethyldisiloxane, 1,3-divinyl-1,1,3,3-tetraphenyldisiloxane and dimethylpolysiloxane with both molecular chain ends blocked by dimethylvinylsiloxy groups. Since these compounds have vinylsilyl groups, they can be subjected to hydrosilylation addition reactions with hydrosilane and organohydrogenpolysiloxane. Particularly, when there are used a bifunctional vinyl silane compound having two vinylsilyl groups in one molecule; and a bifunctional organohydrogenpolysiloxane having two silicon atom-bonded hydrogen atoms (SiH groups) in one molecule, polymerization reaction progresses (i.e. as a result of a chain-extending reaction progressing due to a continuous hydrosilylation addition reaction), thereby making it possible to obtain an organic silicon resin having a molecular weight (polymerization degree) that is high to a certain extent.

However, most of these known vinyl silane compounds generally have vinylsilyl groups that are bonded together by siloxane bonds, which in fact only allows properties derived from siloxane bonds to be imparted to an organic silicon resin (Patent documents 1 and 2; and Non-patent document 1).

PRIOR ART DOCUMENT

Patent Document

Patent document: JP-A-Hei 11-246769
Patent document: JP-A 2013-108063

Non-Patent Document

Non-patent document: "Silicone Handbook" by Kunio Ito, NIKKAN KOGYO SHIMBUN, LTD., Aug. 31, 1990 (first impression of the first edition), pp. 7-11

SUMMARY OF THE INVENTION

Problem to be Solved by the Invention

Therefore, it is an object of the present invention to provide a vinyl silane compound having vinylsilyl groups that are bonded together by a structure other than the siloxane bond such that novel properties can be imparted to an organic silicon resin.

Means to Solve the Problem

The inventors of the present invention diligently conducted a series of studies to achieve the aforementioned objective, and completed the invention as follows. That is, the inventors found that a novel vinyl silane compound having a Diels-Alder reaction product shown below in its structure was useful in solving the abovementioned problem.

Specifically, the present invention is to provide the following vinyl silane compound(s).

[1]
A vinyl silane compound represented by the following formula (1):

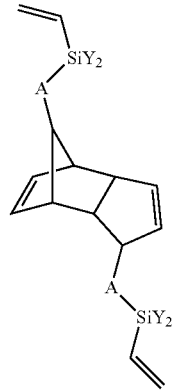

(1)

wherein A independently represents a divalent hydrocarbon group having 1 to 6 carbon atoms; Y independently represents a substituted or unsubstituted monovalent hydrocarbon group having 1 to 12 carbon atoms.

[2]
The vinyl silane compound according to [1], wherein A independently represents a methylene group, an ethylene group or a trimethylene group.

[3]
The vinyl silane compound according to [1] or [2], wherein Y independently represents a methyl group, an ethyl group or a phenyl group.

The vinyl silane compound of the present invention may be a mixture of various vinyl silane compounds with different structures, provided that the structure of the compound of the invention is within the scope of the above formula (1).

Further, the present invention is also to provide the following method(s) for producing the vinyl silane compound.

[4]
A method for producing the vinyl silane compound as set forth in any one of [1] to [3], comprising:
a step of reacting an alkali cyclopentadienylide with a vinyl diorgano (halogen-substituted-organo) silane represented by the following formula (2):

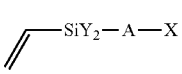

(2)

wherein A represents a divalent hydrocarbon group having 1 to 6 carbon atoms; independently represents a substituted or unsubstituted monovalent hydrocarbon group having 1 to 12 carbon atoms; X represents a halogen atom.

[5]
The method for producing the vinyl silane compound according to [4], wherein A represents a methylene group, an ethylene group or a trimethylene group; Y independently represents a methyl group, an ethyl group or a phenyl group: and X represents a Cl atom or a Br atom.

Effects of the Invention

Since the vinyl silane compound of the invention has vinyl silyl groups, the compound can be subjected to hydrosilylation addition reactions with hydrosilane and organohydrogenpolysiloxane. Particularly, as a result of reacting the vinyl silane compound of the invention with a bifunctional organohydrogenpolysiloxane having in one molecule two silicon atom-bonded hydrogen atoms (SiH groups) (especially, a bifunctional diorganopolysiloxane having a SiH group at each of the two ends of its molecular chain, and optionally containing a small number of branched units in part of the main chain structure while the bifunctional diorganopolysiloxane itself is basically linear), polymerization reaction progresses (i.e. as a result of a chain-extending reaction progressing due to a continuous hydrosilylation addition reaction), thereby making it possible to obtain an organic silicon resin having a molecular weight (polymerization degree) that is high to a certain extent. This organic silicon resin has a thermal plasticity due to the fact that the dicyclopentadiene skeleton from the vinyl silane compound of the invention is capable of being reversibly changed between a dimer and a monomer by heat. Thus, the vinyl silane compound of the present invention is favorable as a compound capable of imparting a thermal plasticity to an organic silicon resin.

BRIEF DESCRIPTION OF THE DRAWINGS

FIG. 1 is a $^1$H-NMR chart of a vinyl silane compound obtained in working example 1.

MODE FOR CARRYING OUT THE INVENTION

The abovementioned vinyl silane compound of the invention is a compound represented by the above general formula (1) (i.e. bis-silane compound having two vinylsilyl groups on the dicyclopentadiene skeleton).

Here, in the above general formula (1), it is preferred that a divalent hydrocarbon group represented by A and having 1 to 6, especially 1 to 4, particularly 1 to 3 carbon atoms be a linear alkylene group represented by —(CH$_2$)$_n$— (n represents an integer of 1 to 6, especially 1 to 4, particularly 1 to 3). Among these groups, particularly preferred is a methylene group represented by —(CH$_2$)—, an ethylene group (dimethylene group) represented by —(CH$_2$)$_2$—, or a trimethylene group represented by —(CH$_2$)$_3$—.

Next, in the above general formula (1), examples of a substituted or unsubstituted monovalent hydrocarbon group represented by Y and having 1 to 12, preferably 1 to 6 carbon atoms include: alkyl groups such as a methyl group, an ethyl group, a propyl group, an isopropyl group, a butyl group, an isobutyl group, a tert-butyl group, a pentyl group, a hexyl group, a heptyl group, an octyl group, a 2-ethylhexyl group, a nonyl group, a decyl group and a dodecyl group; cycloalkyl groups such as a cyclopentyl group and a cyclohexyl group; alkenyl groups such as a vinyl group, an allyl group, a propenyl group, an isopropenyl group, a butenyl group, an isobutenyl group, a pentenyl group, a hexenyl group and a cyclohexenyl group; aryl groups such as a phenyl group, a tolyl group, a xylyl group and an α-, β-naphthyl group; aralkyl groups such as a benzyl group, a 2-phenylethyl group and a 3-phenylpropyl group; or groups obtained by substituting a part of or all the hydrogen atoms in any of these groups with, for example, a cyano group and/or halogen atoms such as F, Cl and Br, the examples of such substituted groups including a 3-chloropropyl group, a 3,3,3-trifluoropropyl group and a 2-cyanoethyl group. Among the above groups, as a monovalent hydrocarbon group having 1 to 6 carbon atoms, a methyl group and a phenyl group are preferred, among which a methyl group is particularly preferred.

The vinyl silane compound of the invention can be easily produced by, for example, the following method. That is, the compound of the invention may be produced by reacting, in an organic solvent, an alkali cyclopentadienylide with a vinyl diorgano (halogen-substituted-organo) silane represented by the following formula (2):

[Chemical formula 3]

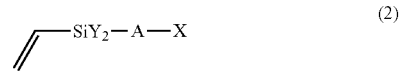

(2)

In this formula, A represents a divalent hydrocarbon group having 1 to 6, especially 1 to 4, particularly 1 to 3 carbon atoms, such as a methylene group, an ethylene group, a trimethylene group and a tetramethylene group, among which a methylene group, an ethylene group or a trimethylene group is preferred; Y independently represents a substituted or unsubstituted monovalent hydrocarbon group having 1 to 12, preferably 1 to 6 carbon atoms, and it is more preferred that Y independently represent a methyl group or an ethyl group; X represents a halogen atom such as F, Cl, Br and I, preferably a Cl atom or a Br atom.

Examples of the alkali cyclopentadienylide used in the production method of the invention include sodium or potassium salts of cyclopentadiene, such as sodium cyclopentadienylide and potassium cyclopentadienylide.

It is preferred that such alkali cyclopentadienylide be used in an amount of 1.0 to 2.0 mol, particularly preferably 1.0 to 1.2 mol, per 1 mol of the vinyl diorgano (halogen-substituted-organo) silane.

Further, examples of a favorable organic solvent used in the production method of the invention include aromatics such as benzene, toluene and xylene; ethers such as diethyl ether, diisopropyl ether and tetrahydrofuran; and hydrocarbons such as n-pentane, n-hexane and cyclohexane.

There are no particular restrictions on a reaction temperature in the production method of the invention, as long as the temperature is that at which Diels-Alder reaction in the alkali cyclopentadienylide may progress. When the reaction temperature is 150° C. or higher, a dimer produced may turn into a monomer due to thermal decomposition. Thus, it is preferred that the reaction temperature be room temperature (25° C.±10° C.) to 100° C.

After the reaction is finished, the target compound is then purified by, for example, distillation under a reduced pressure to obtain the target compound of the present invention.

Working Example

The present invention is described in detail hereunder with reference to working and reference examples. However, the invention is not limited to the following working examples.

Working Example 1

Vinyldimethylchloromethylsilane of 94.3 g (0.7 mol) and tetrahydrofuran of 100 ml were put into a 1,000 ml fournecked flask, followed by cooling them to 0° C. Next, 350 ml (0.7 mol) of a 2.0 M tetrahydrofuran solution of sodium cyclopentadienylide (by Sigma-Aldrich) was delivered thereinto by drops while performing stirring. After dropping was finished, the temperature was raised to 50° C., and stirring was then performed for 12 hours. After the reaction was stopped by adding a saturated aqueous solution of ammonium chloride, an organic layer was separated, and a solvent was then distilled away under a reduced pressure, followed by purifying the target product by distillation under a reduced pressure to obtain 35.4 g (30%) of a colorless and transparent liquid having a boiling point of 51° C./300 Pa.

The $^1$H-NMR spectrum of the product was measured to confirm the structure thereof (FIG. 1)

Based on the result of the $^1$H-NMR measurement, the product obtained was considered to be 3a,4,7,7a,-tetrahydro-1,8-bis(vinyldimethylsilylmethyl)-4,7-methano-1H-indene having a structure represented by a formula (3).

[Chemical formula 4]

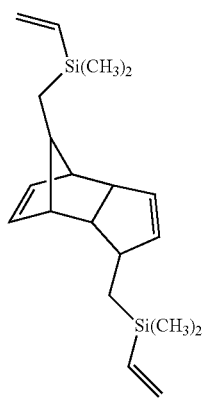

(3)

Reference Example 1

In this example, 0.8 parts by mass (simply referred to as "part(s)" hereafter) of the vinyl silane prepared in working example 1 were added to 7.4 parts of a dimethylpolysiloxane with a number of repetitions of dimethylsiloxane units being approximately 40 on the main chain thereof, and with both the molecular chain ends thereof being blocked by dimethylhydrogensiloxy groups (dimethylpolysiloxane with both molecular chain ends blocked by dimethylhydrogensiloxy groups). After mixing them at room temperature (i.e. 25° C., the same applies hereinafter) for 5 min, a platinum catalyst of 0.1 parts (CAT-PL-50T by Shin-Etsu Chemical Co., Ltd.) was added thereto, followed by mixing them again at room temperature for another 5 min. The mixture obtained was then heated in a glass petri dish at 60° C. for 48 hours to obtain a cured product 1.

Reference Example 2

In this example, 0.8 parts of the vinyl silane prepared in working example 1 were added to 11.5 parts of a dimethylpolysiloxane with a number of repetitions of dimethylsiloxane units being approximately 60 on the main chain thereof, and with both the molecular chain ends thereof being blocked by dimethylhydrogensiloxy groups (dimethylpolysiloxane with both molecular chain ends blocked by dimethylhydrogensiloxy groups). After mixing them at room temperature for 5 min, the platinum catalyst of 0.1 parts (CAT-PL-50T by Shin-Etsu Chemical Co., Ltd.) was added thereto, followed by mixing them again at room temperature for another 5 min. The mixture obtained was then heated in a glass petri dish at 60° C. for 48 hours to obtain a cured product 2.

Comparative Reference Example 1

In this example, 0.5 parts of 1,3-divinyl-1,1,3,3-tetramethyldisiloxane were added to 11.5 parts of the dimethylpolysiloxane with a number of repetitions of dimethylsiloxane units being approximately 60 on the main chain thereof, and with both the molecular chain ends thereof being blocked by dimethylhydrogensiloxy groups (dimethylpolysiloxane with both molecular chain ends blocked by dimethylhydrogensiloxy groups). After mixing them at room temperature for 5 min, the platinum catalyst of 0.1 parts (CAT-PL-50T by Shin-Etsu Chemical Co., Ltd.) was added thereto, followed by mixing them again at room temperature for another 5 min. The mixture obtained was then heated in a glass petri dish at 60° C. for 48 hours to obtain a cured product 3.

(Test)

The cured products 1 to 3 prepared in reference examples 1 and 2; and comparative reference example 1 were placed on an aluminum petri dish, and then heated in an oven at 180° C. for an hour. After heating, the properties of the cured products 1 to 3 were confirmed by visual observation and finger touch (i.e. whether the cured products were still solid, or had liquefied due to heating). In addition, with regard to the cured products 1 and 2 that had liquefied due to heating, the cured products were further left under room temperature so as to confirm, by visual observation and finger touch, whether the properties thereof would change (i.e. whether what had once liquefied due to heating would solidify again).

These results are shown in the following Table 1.

TABLE 1

|  | Reference example 1 Cured product 1 | Reference example 2 Cured product 2 | Comparative reference example 1 Cured product 3 |
|---|---|---|---|
| Before heating | Solid | Solid | Solid |
| After heating | Liquid | Liquid | Solid (No change in property) |
| Time elapsed until fluidity again disappeared at room temperature | 2 Days | 1 Day | — |

According to the results in Table 1, it is clear that each of the vinyl silane compounds used in reference examples 1 and 2 can be reversibly changed between a dimer and a monomer by heat, such that a thermal plasticity can thus be imparted to an organic silicon resin, which has been impossible with the conventional vinyl silane compounds.

However, the present invention is not limited to the aforementioned embodiments. The above embodiments are provided as examples, and any embodiment shall be included in the technical scope of the invention, provided that such embodiment has a structure that is substantially identical to the technical ideas described in the claims of the invention, and that the embodiment brings about similar functions and effects.

INDUSTRIAL APPLICABILITY

Since the vinyl silane compound of the invention has vinylsilyl groups, hydrosilylation addition reactions with hydrosilane and organohydrogenpolysiloxane are possible. Particularly, as a result of reacting the vinyl silane compound of the invention with a bifunctional organohydrogenpolysiloxane having in one molecule two silicon atom-bonded hydrogen atoms (SiH groups), polymerization reaction progresses (i.e. as a result of a chain-extending reaction progressing due to a continuous hydrosilylation addition reaction), thereby making it possible to obtain an organic silicon resin having a molecular weight (polymerization degree) that is high to a certain extent. This organic silicon resin has a thermal plasticity due to the fact that the dicyclopentadiene skeleton from the vinyl silane compound of the invention is capable of being reversibly changed between a dimer and a monomer by heat. Therefore, the vinyl silane compound of the present invention is useful as a compound for imparting a thermal plasticity to an organic silicon resin.

The invention claimed is:

1. A vinyl silane compound represented by formula (1):

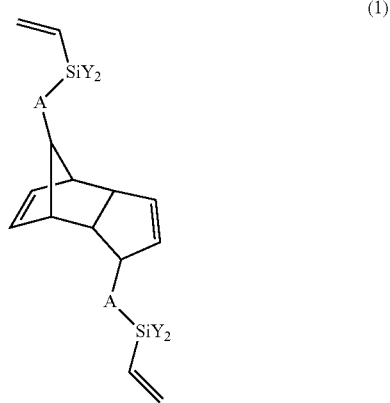

(1)

wherein A independently at each instance represents a divalent hydrocarbon group having 1 to 6 carbon atoms; and Y independently at each instance represents a substituted or unsubstituted monovalent hydrocarbon group having 1 to 12 carbon atoms.

2. The vinyl silane compound according to claim 1, wherein A independently at each instance represents a methylene group, an ethylene group or a trimethylene group.

3. The vinyl silane compound according to claim 1, wherein Y independently at each instance represents a methyl group, an ethyl group or a phenyl group.

4. A method for producing the vinyl silane compound of claim 1, comprising:
reacting an alkali cyclopentadienylide with a vinyl diorgano (halogen-substituted-organo) silane represented by formula (2):

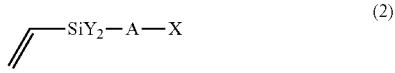

(2)

wherein A represents a divalent hydrocarbon group having 1 to 6 carbon atoms; Y independently at each instance represents a substituted or unsubstituted monovalent hydrocarbon group having 1 to 12 carbon atoms; and X represents a halogen atom.

5. The method for producing the vinyl silane compound according to claim 4, wherein A represents a methylene group, an ethylene group or a trimethylene group; Y independently at each instance represents a methyl group, an ethyl group or a phenyl group; and X represents a Cl atom or a Br atom.

6. The vinyl silane compound according to claim 2, wherein Y independently at each instance represents a methyl group, an ethyl group or a phenyl group.

7. A method for producing the vinyl silane compound of claim 2, comprising:
reacting an alkali cyclopentadienylide with a vinyl diorgano (halogen-substituted-organo) silane represented by formula (2):

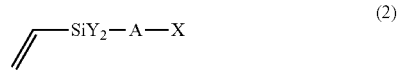

(2)

wherein A represents a divalent hydrocarbon group having 1 to 6 carbon atoms; Y independently at each instance represents a substituted or unsubstituted monovalent hydrocarbon group having 1 to 12 carbon atoms; and X represents a halogen atom.

8. A method for producing the vinyl silane compound of claim 3, comprising:
reacting an alkali cyclopentadienylide with a vinyl diorgano (halogen-substituted-organo) silane represented by formula (2):

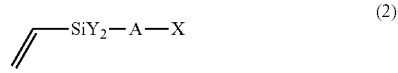

(2)

wherein A represents a divalent hydrocarbon group having 1 to 6 carbon atoms; Y independently at each instance represents a substituted or unsubstituted monovalent hydrocarbon group having 1 to 12 carbon atoms; and X represents a halogen atom.

9. A method for producing the vinyl silane compound of claim 6, comprising:
reacting an alkali cyclopentadienylide with a vinyl diorgano (halogen-substituted-organo) silane represented by the formula (2):

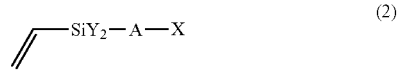

(2)

wherein A represents a divalent hydrocarbon group having 1 to 6 carbon atoms; Y independently at each instance represents a substituted or unsubstituted monovalent hydrocarbon group having 1 to 12 carbon atoms; and X represents a halogen atom.

10. The method for producing the vinyl silane compound according to claim 7, wherein A represents a methylene group, an ethylene group or a trimethylene group; Y independently at each instance represents a methyl group, an ethyl group or a phenyl group; and X represents a Cl atom or a Br atom.

11. The method for producing the vinyl silane compound according to claim 8, wherein A represents a methylene group, an ethylene group or a trimethylene group; Y independently at each instance represents a methyl group, an ethyl group or a phenyl group; and X represents a Cl atom or a Br atom.

12. The method for producing the vinyl silane compound according to claim 9, wherein A represents a methylene group, an ethylene group or a trimethylene group; Y independently at each instance represents a methyl group, an ethyl group or a phenyl group; and X represents a Cl atom or a Br atom.

* * * * *